US012729400B2

(12) United States Patent
Corioni et al.

(10) Patent No.: US 12,729,400 B2
(45) **Date of Patent: *Sep. 8, 2026**

(54) SEQUENCING METHOD FOR GENOMIC REARRANGEMENT DETECTION

(71) Applicant: Agilent Technologies, Inc., Santa Clara, CA (US)

(72) Inventors: Margherita Corioni, Sunnyvale, CA (US); Douglas N Roberts, Campbell, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 510 days.

This patent is subject to a terminal disclaimer.

(21) Appl. No.: 17/875,153

(22) Filed: Jul. 27, 2022

(65) Prior Publication Data

US 2022/0364169 A1 Nov. 17, 2022

Related U.S. Application Data

(63) Continuation of application No. 15/648,240, filed on Jul. 12, 2017, now Pat. No. 11,505,826.

(51) Int. Cl.
*C12Q 1/6874* (2018.01)
*C12Q 1/6806* (2018.01)

(52) U.S. Cl.
CPC ......... *C12Q 1/6874* (2013.01); *C12Q 1/6806* (2013.01)

(58) Field of Classification Search
CPC ................ C12Q 1/6874; C12Q 1/6806; C12Q 2525/155; C12Q 2525/191; C12Q 2535/122; C12Q 2535/125; C12Q 2563/179
See application file for complete search history.

(56) References Cited

U.S. PATENT DOCUMENTS 5,948,902 A 9/1999 Honkanen et al.
2006/0073506 A1 4/2006 Christians et al.
2006/0177833 A1 8/2006 Brenner et al.
2009/0181375 A1 7/2009 Peter et al.
2010/0069263 A1 3/2010 Shendure et al.
2010/0227329 A1 9/2010 Cuppens et al.
2010/0279890 A1 11/2010 Lothe et al.
2012/0071331 A1 3/2012 Casbon et al.
2012/0164630 A1 6/2012 Porreca et al.
2012/0309633 A1 12/2012 Van Eijk et al.
2014/0120540 A1 5/2014 Seligmann et al.
2014/0234847 A1 8/2014 Alt et al.
2014/0272956 A1 9/2014 Huang et al.
2014/0315199 A1 10/2014 Rhodes et al.
2015/0044687 A1 2/2015 Schmitt et al.
2015/0087535 A1 3/2015 Patel
2015/0132763 A1 5/2015 Amorese et al.
2015/0211050 A1 * 7/2015 Lafrate ................ C12Q 1/6809 506/2
2015/0284712 A1 10/2015 Kurihara et al.
2016/0017320 A1 1/2016 Wang et al.
2016/0046986 A1 2/2016 Eltoukhy et al.
2016/0053303 A1 2/2016 Brenner et al.
2016/0215333 A1 7/2016 Papadopoulos et al.

FOREIGN PATENT DOCUMENTS

EP 2990493 A1 3/2016
JP 2015517307 A 6/2015
JP 2017504347 A 2/2017
JP 2017050847 A 3/2017
JP 2017079735 A 5/2017
KR 1020160141680 A 12/2016
WO 2007133831 A2 11/2007
WO WO-2012162267 A2 * 11/2012 ............. C12N 15/10
WO 2013169339 A1 11/2013
WO 2014172529 A1 10/2014
WO 2014200926 A2 12/2014
WO 2015103287 A2 7/2015
WO 2015112974 A1 7/2015
WO 2015148219 A1 10/2015

OTHER PUBLICATIONS

Fromenty et al. (Biochimica et Biophysica Acta (BBA)-Gene Structure and Expression 1308.3 (1996): 222-230.) (Year: 1996).*
"HiSeq 2500 Sequencing System: Specification Sheet," Illumina, Mar. 27, 2015, 4 pages.
"Ion AmpliSeq TM Library Kit 2.0 User Guide," Publication No. MAN0006735, May 24, 2017, 91 pages.
"TruSeq® Custom Amplicon v 1.5 Reference Guide," Illumina, Feb. 2016, 42 pages.
Agilent Technologies, Inc., et al., "HaloPlex HS Target Enrichment System for Illumina Sequencing Protocol," Version C1, Agilent Technologies, Inc., Dec. 2016, 1-63.
Agilent Technologies, Inc., et al., "HaloPlex Target Enrichment System for Illumina Sequencing," Version F1, Agilent Technologies, Inc., Jul. 2015, 1-65.
Agilent Technologies, Inc., et al., "SureSelect QXT Target Enrichment for Illumina Multiplexed Sequencing," Version D1, Agilent Technologies, Inc., Dec. 2016, 1-77.
Agilent Technologies, Inc., et al., "SureSelect XT Target Enrichment System for Illumina Paired-End Multiplexed Sequencing Library," Version C1, Agilent Technologies, Inc., Jul. 2017, 1-98.
EPO, et al., "Extended European Search Report mailed on Mar. 19, 2021," Application No. 18832317.4, 11 pages.

(Continued)

*Primary Examiner* — Sahana S Kaup

(57) ABSTRACT

The present disclosure is directed to a single-end sequencing method for improved detection of genomic rearrangements such as deletions, insertions, inversions, and translocations that are present in a polynucleotide. A first priming event allows for sequencing of a target sequence, and a second priming event on an adapter allows for identification of the sequences amplified and tagged by selective amplification. The combination of priming events in the same direction facilitates read alignment and the identification of any genomic rearrangements.

17 Claims, 2 Drawing Sheets

(56) References Cited

OTHER PUBLICATIONS

Ernani, et al., "Agilent's SureSelect Target Enrichment System: Bringing Cost and Process Efficiency to Next-generation Sequencing," Agilent Technologies, Mar. 16, 2009, 8 pages.
Fromenty, Bernard et al., "Efficient And Specific Amplification Of Identified Partial Duplications Of Human Mitochondrial DNA by Long PCR," Biochimica et Biophysica Acta (BBA)-Gene Structure and Expression; vol. 1308, 1996, 222-230.
Glanville, J et al., "Deep Sequencing In Library Selection Projects: What Insight Does It Bring?" Current Opinion in Structural Biology, vol. 33, Aug. 1, 2015, 146-160.
Illumina, et al., "HiSeq® 3000/4000 Sequencing Systems: Specification Sheet," Illumina, Nov. 16, 2015, 4 pages.
Illumina, et al., "MiSeq® System: Specification Sheet," Illumina, May 17, 2016, 4 pages.
Illumina, et al., "NextSeq 550 Sequencing System," Illumina, Sep. 6, 2017, 4 pages.
Illumina, et al., "NextSeq System: Custom Primers Guide," Illumina, Oct. 2015, 10 pages.
Illumina, et al., "TruSeq Custom Enrichment Kit," Illumina, Nov. 14, 2014, 4 pages.
Illumina_Techsupport_Session15, et al., "Library of Sequencer Setup with Dual Index," <URL,https://jp.illumina.com/content/dam/illumina/marketing/apac/japan/documents/pdf/2013_illumina_techsupport_session15.pdf >, [online], 2012, 2013, 61 pages.
Lllumina, et al., "SureSelect Target Enrichment System," Illumina Single-End Sequencing Platform Library Prep, Version 2.0, Dec. 2009, 1-56.
Padilla, R et al., "PCR-based targeted sequence enrichment for next generation sequencing platform," Life Technologies Corporation, Jun. 8, 2010, 1 page.
PCT, "International Search Report and Written Opinion mailed on Feb. 28, 2019," Application No. PCT/US2018/041435, 13 pages.
Peng, Quan et al., "Reducing Amplification Artifacts In High Multiplex Amplicon Sequencing By Using Molecular Barcodes," BMC Genomics, vol. 16, No. 589, Aug. 7, 2015, 1-12.
Zheng, Zongli et al., "Anchored Multiplex PCR For Targeted Next-Generation Sequencing," Nature Medicine, vol. 20, No. 12, Nov. 10, 2014, 1479-1484.

* cited by examiner

SEQUENCING METHOD FOR GENOMIC REARRANGEMENT DETECTION

CROSS-REFERENCE TO RELATED APPLICATIONS

This application is a continuation of U.S. patent application Ser. No. 15/648,240, filed Jul. 12, 2017, the contents of which are incorporated herein by reference.

FIELD OF THE INVENTION

The present disclosure relates to sequencing methods, compositions and kits for improved detection of genomic rearrangements such as fusion genes. The present disclosure also relates to library preparation methods of target polynucleotides comprising genomic rearrangements.

BACKGROUND

The ability to identify genomic rearrangements using nucleic acid sequencing methods has proven greatly beneficial in the detection of human genetic disorders and diseases. Genomic rearrangements generally refers to any rearrangement of nucleotides in a nucleic acid chain including deletion, insertion, inversion, or translocation of one or more nucleotides, and can be detected by sequencing the nucleic acid of interest and comparing sequence data to a reference such as a known nucleic acid sequence. Next Generation Sequencing (NGS) can be used to rapidly analyze polynucleotides and to detect any genomic rearrangements in a polynucleotide. NGS allows for parallel analysis of a great number of sequences simultaneously. In some formats, a polynucleotide such as DNA is affixed to a solid surface via one or more adapters and amplified to increase signal strength. In general, a library is prepared for sequencing by fragmentation of a sample into polynucleotide fragments, tagging the fragments with one or more adapters, and amplification of the polynucleotide fragments. The fragments can be amplified with one or more amplification primers. In sequencing by synthesis formats, the fragments hybridize with sequencing primers, and labeled dideoxynucleotides are added enzymatically. The signals from the labeled dideoxynucleotides are detected and analyzed to determine the sequence.

A polynucleotide of interest may be analyzed using a single-end or paired-end sequencing method. Single-end sequencing methods involve sequencing of a genomic fragment from one end of the fragment towards the opposite end. A single-end sequencing read provides one read per fragment corresponding to n base pairs of one of the two ends of the fragment, where n is the number of sequencing cycles. Single-end sequencing is typically not well-suited for detection of large-scale genomic rearrangements and repetitive sequence elements. Single-end reads that span the fusion junctions provide base-pair evidence for the fusion events. However it can be difficult to ensure that the single-end read has proceeded to a sufficient number of base-pairs to identify a fusion event.

Paired-end methods involve reading of a nucleic acid fragment from one end to the other end up to a specified read length, and then another round of reading from the opposite side of the fragment. For paired-end methods, a forward sequence read and a reverse sequence read is performed and the data paired into adjoining sequences. The sequences are matched with the reference sample to identify variants. Paired-end sequencing methods are commonly used to detect genomic rearrangements because such methods generally provide good positioning information, making it easier to resolve structural rearrangements present in the genome. However, many sequencing instruments are not configured to perform paired-end sequencing and are only single-end sequencing enabled.

WO 2007133831A2 discusses methods and compositions for acquiring nucleotide sequence information of target sequences using adaptors interspersed in target polynucleotides. The methods can be used for inserting a plurality of adaptors at spaced locations within a target polynucleotide or fragment. The adaptors may serve as platforms for interrogating adjacent sequences using various sequencing chemistries, such as those that identify nucleotides by primer extension, probe ligation, and the like. The disclosure encompasses methods and compositions for the insertion of known adaptor sequences into target sequences, such that there is an interruption of contiguous target sequence with the adaptors. The disclosure states that by sequencing both "upstream" and "downstream" of the adaptors, identification of entire target sequences may be accomplished.

WO2015112974A1 discusses aspects relating to methods for preparing and analyzing nucleic acids. In some embodiments, methods for preparing nucleic acids for sequence analysis (e.g., using next-generation sequencing) are provided.

WO2015148219A1 discusses a method for analyzing a target nucleic acid fragment, comprising generating a first strand using one strand of the target as a template by primer extension, using a first oligonucleotide primer which comprises, from 5' to 3', an overhang adaptor region, a primer ID region, a sequencing primer binding site, and a target specific sequence region complementary to one end of the target fragment; optionally removing non-incorporated primers; amplifying the target from the generated first strand to produce an amplification product; and detecting the amplification product. The disclosure also discusses why unique primers are useful for such target analysis methods.

An improved method for detection of genomic rearrangements using single-end sequencing would be a useful contribution to the field, particularly if the method has utility in combination with high-throughput sequencing analysis.

SUMMARY OF THE INVENTION

Methods, compositions and kits are provided for detecting genomic rearrangements in polynucleotides. The present methods, compositions and kits can be used to more easily and reliably detect genomic rearrangements utilizing single-end sequencing of nucleic acids of interest.

These and other features and advantages of the present invention will be apparent from the following detailed description, in conjunction with the appended claims.

BRIEF DESCRIPTION OF THE DRAWING

The present teachings are best understood from the following detailed description when read with the accompanying drawing figures. The features are not necessarily drawn to scale.

DEFINED TERMINOLOGY

Figure 1:
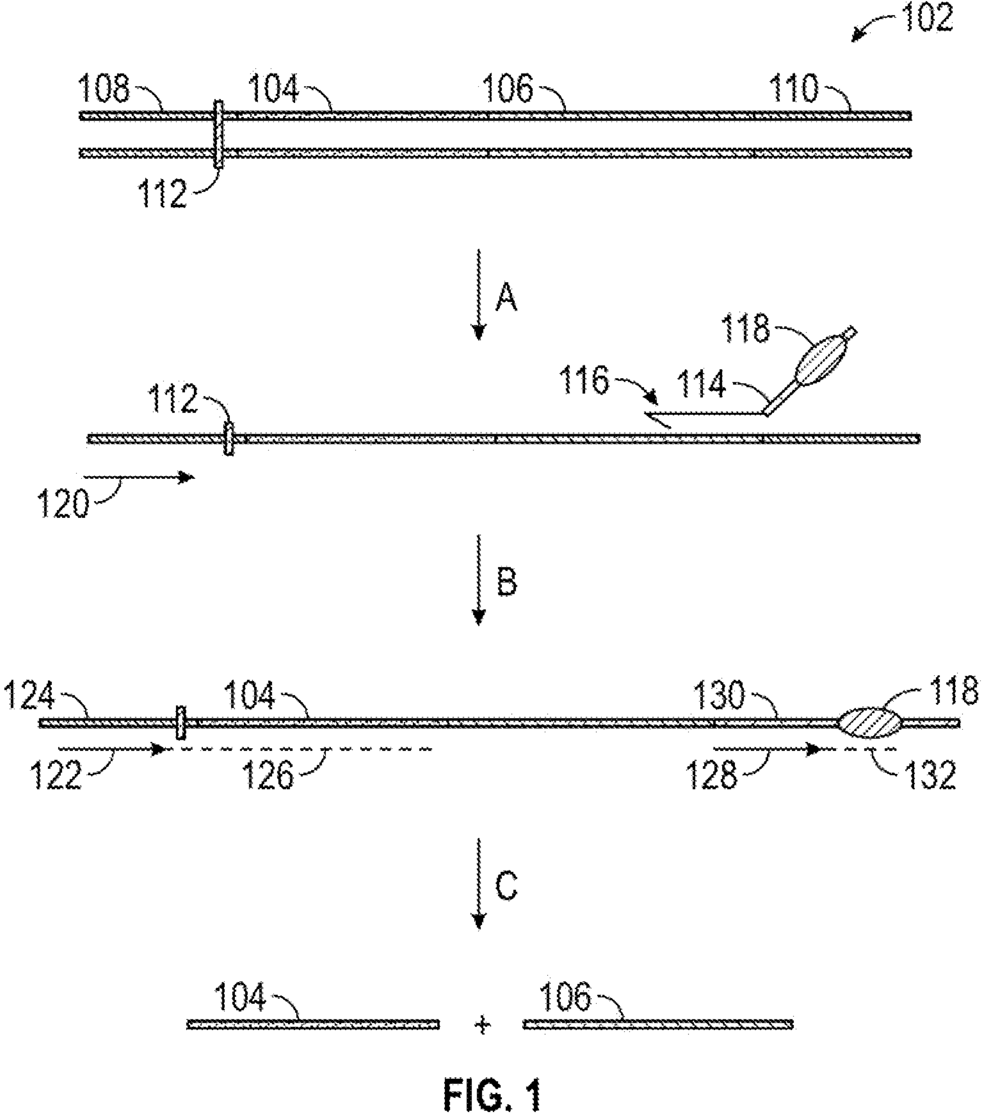
FIG. 1 illustrates an embodiment of the methods of preparing polynucleotides for sequencing.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.7 to 1.15. For example, "approximately the same" means that one of ordinary skill in the art considers the items being compared to be the same.

The term "polynucleotide" and "nucleic acid" are used interchangeably herein to describe a polymer of any length, e.g., greater than about 10 bases, greater than about 100 bases, greater than about 500 bases, greater than 1000 bases, up to about 10,000 or more bases, composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, and thymine (G, C, A, and T, respectively). As used in the specification and appended claims, a polynucleotide can be an adapted polynucleotide, a polynucleotide amplicon, or an adapted polynucleotide amplicon, unless indicated otherwise. An adapted polynucleotide differs from a polynucleotide of interest in that an adapter has been added to the polynucleotide of interest.

As used herein, the term "target nucleic acid" or "target" refers to a nucleic acid containing a target nucleic acid sequence. A target nucleic acid may be single-stranded or double-stranded, and often is double-stranded DNA. A "target nucleic acid sequence," "target sequence" or "target region," as used herein, means a specific sequence or the complement thereof. A target sequence may be within a nucleic acid in vitro or in vivo within the genome of a cell, which may be any form of single-stranded or double-stranded nucleic acid.

"Hybridization" or "hybridizing" refers to a process where completely or partially complementary nucleic acid strands come together under specified hybridization conditions to form a double-stranded structure or region in which the two constituent strands are joined by hydrogen bonds. Although hydrogen bonds typically form between adenine and thymine or uracil (A and T or U) or cytosine and guanine (C and G), other base pairs may form (e.g., Adams et al., "The Biochemistry of the Nucleic Acids," 11th ed., 1992).

The term "primer" means an oligonucleotide, either enzymatically made or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. A primer serves as an initiation point for nucleotide polymerization catalyzed by either DNA polymerase, RNA polymerase, or reverse transcriptase. A primer may be 4-1000 bases or more in length, e.g., 10-500 bases.

As used herein, the term "primer extension" refers to extension of a primer by annealing specific oligonucleotides to the primer using a polymerase. The term "adapter" refers to a nucleic acid molecule attached to a polynucleotide of interest to form a synthetic polynucleotide. An adapter can be single stranded or double stranded, and it can comprise DNA, RNA, and/or artificial nucleotides. An adapter can be located at an end of a polynucleotide of interest, or it can be located in a middle or interior portion. The adapter can add one or more functionalities or properties to the polynucleotide of interest, such as providing a priming site for amplification or sequencing or adding a barcode. By way of example, adapters can include a universal primer and/or a universal priming site, including a priming site for sequencing. By way of further example, adapters can contain one or more barcodes of various types or for various purposes, such as molecular barcodes, sample barcodes and/or target-specific barcodes. Various adapters are known in the field and can be used or modified for use in the present methods, compositions and kits. For instance, adapters include Y adapters which can be attached to polynucleotides to produce libraries with varying 5' ends. Adapters may also include separate sequence (for example AB adapters) in which an A adapter is attached to one end of a polynucleotide and a B adapter is attached to an opposite end of the polynucleotide. Adapters also include stem-loop adapters, in which a hairpin loop is attached to an end of the polynucleotide; a portion (typically the stem) can be cleaved before amplification or sequencing. An adapter can be attached to a polynucleotide of interest by any suitable technique, including, but not limited to ligation, use of a transposase, hybridization, and/or primer extension. For example, adapters may be ligated to ends of a polynucleotide of interest. As another example, adapters are attached by using a transposase to insert transposons comprising adapters into a polynucleotide of interest, thereby providing adapters at the ends of fragments of a polynucleotide of interest. In some embodiments, an adapter comprises a target-specific primer and a target-specific barcode, which allows the attachment of an adapter to the polynucleotide of interest (more particularly, to a complementary polynucleotide) by primer extension of the target-specific primer.

The term "sequencing" refers to determining the identity of one or more nucleotides, i.e., whether a nucleotide is a G, A, T, or C.

The term "single-end sequencing" means determining the sequence of a polynucleotide using reads from one end of the polynucleotide ("single-end reads"). Single-end reads can be performed by any sequencing process, including next-generation sequencing and other massively parallel sequencing techniques. Instruments configured to perform single-end sequencing are commercially available from a number of companies. For example, the Hiseq 2500 from Illumina has single-end 50 bp and single-end 100 bp read lengths available. In some embodiments the nominal, average, mean or absolute length of single-end reads is at least 20 contiguous nucleotides, alternatively at least 30 contiguous nucleotides, alternatively at least 40 contiguous nucleotides, alternatively at least 50 contiguous nucleotides. In some embodiments the nominal, average, mean or absolute length of single-end reads is at most 300 contiguous nucleotides, at most 200 contiguous nucleotides, alternatively at most 150 contiguous nucleotides, alternatively at most 120 contiguous nucleotides, alternatively at most 100 contiguous nucleotides. The foregoing minimums and maximums can be combined to form a range.

As used herein, the term "portion" or "fragment" of a sequence refers to any portion of the sequence (e.g., a nucleotide subsequence or an amino acid subsequence) that is smaller than the complete sequence. Portions of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length.

The term "fusion gene" refers to a polynucleotide formed from two previously separate genes. A fusion gene can result from a translocation, interstitial deletion, or chromosomal inversion, and they are frequently found in human cancer cells. Fusion genes may result in the expression of a fusion transcript which is translated into a fusion protein that alters the normal regulatory pathways of cells and/or promotes growth of cancer cells. Gene variants may also result in aberrant proteins that affect normal regulatory pathways. Many fusion genes polynucleotides are known and more are being discovered. For example, US20100279890, US20140120540, US20140272956, and US20140315199 disclose many fusion genes associated with cancer and other diseases, as well as methods of detecting such fusion genes. The present methods, compositions and kits can be used to detect known gene fusion, but may be used to discover previously unknown gene fusions.

As used herein, the term "priming site" refers to a site within an oligonucleotide or polynucleotide configured for hybridizing to a primer, so that adjacent sequences, or sequences of sufficient proximity for single-end sequencing, can be amplified or sequenced such as by primer extension. A priming site can be a sequence that occurs in a polynucleotide of interest or a sequence that is added to a polynucleotide by adding an adapter comprising the priming site. An adapter containing a priming site can be added by ligation, by use of a transposase, by primer extension, or by other techniques.

In the present disclosure, numeric ranges are inclusive of the numbers defining the range. In the present disclosure, wherever the word "comprising" is found, it is contemplated that the words "consisting essentially of" or "consisting of" may be used in its place. It should be recognized that chemical structures and formula may be elongated or enlarged for illustrative purposes.

As used in the specification and appended claims, the terms "a", "an," and "the" include both singular and plural referents, unless the context clearly dictates otherwise. Thus, for example, "a primer" includes one primer and plural primers. In the present disclosure, ordinal numbers such as terms first, second, third, and so on do not mean that a first event occurs before a second event (unless the context indicates otherwise); instead they are used to distinguish different events from each other.

Unless defined otherwise, all technical and scientific terms used herein have the same meaning as commonly understood by those working in the fields to which this disclosure pertain.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

All patents and publications referred to herein are expressly incorporated by reference. The citation of any publication is for its disclosure prior to the filing date and should not be construed as an admission that the present claims are not entitled to antedate such publication. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

DETAILED DESCRIPTION

In some embodiments, the present disclosure provides a method of preparing a polynucleotide for sequencing by attaching a target-specific barcode. The method comprises amplifying a polynucleotide with a first amplification primer and a second amplification primer, wherein the first amplification primer comprises a first priming sequence and a target-specific barcode, wherein the first priming sequence hybridizes to a first priming site of the polynucleotide. This amplification generates polynucleotide amplicons, wherein the polynucleotide amplicons comprise sequences identical or complementary to the polynucleotide of interest and the target-specific barcode.

The first amplification primer comprises a first amplification primer which is target-specific (that is, it is complementary to and/or hybridizes with a target sequence within the adapted polynucleotide). The first amplification primer further comprises a target-specific barcode, which is a barcode specific to a target sequence, for example, a barcode specific to a portion of a gene, such as a portion of a fusion gene. The amplification generates polynucleotide amplicons, wherein the polynucleotide amplicons comprise sequences identical or complementary to the polynucleotide of interest and the target-specific barcode. The second amplification primer hybridizes to (1) a portion of an adapter attached to the polynucleotide at a distance from the first priming site, or (2) a second priming site of the polynucleotide, wherein the second priming site is at a distance from the first priming site. In some embodiments, the method can further comprise attaching an adapter to a polynucleotide to form an adapted polynucleotide, wherein the adapter comprises a second priming site and optionally an adapter barcode. In some embodiments, the second priming site is on the adapter and is a universal priming site and/or a site for a sequencing primer, and/or the second primer binding site is a universal priming site at a 5' end of an adapted polynucleotide. In some embodiments, the adapter and/or the second priming site is at a 5' end of a strand of the polynucleotide, and the first priming site is at a 3' end of the strand. In some embodiments, the adapter barcode is a sample barcode or a molecular barcode. A molecular barcode can be a unique sequence, in that it is unique within a set of adapters attached to a pool of polynucleotides of interest.

In some embodiments, the present disclosure provides methods, compositions and kits for preparing a library of polynucleotides for sequencing by attaching a target-specific barcode. A pool of polynucleotides is amplified using a first set of amplification primers and a second set of amplification primers, wherein a first set of amplification primers hybridize to a plurality of different sequences within the pool of polynucleotide, wherein each of the first set of amplification primers comprises a different target-specific barcode. In some embodiments, adapters comprising an adapter barcode are attached to polynucleotide amplicons. The second set of amplification primers hybridizes to (1) a portion of an adapter attached to the polynucleotide at a distance from the first priming site, or (2) a second priming site of the polynucleotide, wherein the second priming site is at a distance from the first priming site. Amplification with the first and second sets of primers generates a library of polynucleotides amplicons. Adapters can be added to the polynucleotide amplicon. In some embodiments, the adapter is added before the amplification, and the adapter comprises a second priming site that hybridizes to the second set of amplification primers. In some embodiments, the adapters are added after amplification, for example to provide a sequencing priming site on the polynucleotide amplicons.

Each of the plurality of polynucleotide amplicons can be sequenced at two locations by performing a first primer extension and a second primer extension, wherein the sequencing of the first primer extension and the second primer extension are performed in the same direction for each of the adapted polynucleotide amplicons. A genomic rearrangement can be identified based on data generated from the sequencing of the first primer extension and the second primer extension.

In other embodiments, the present disclosure provides compositions and kits for detecting a genomic rearrangement in a polynucleotide having a first binding site. The compositions and kits comprise first and second amplification primers. The first amplification primer comprises a target-specific primer and a target-specific barcode. The compositions and kits can further comprise an adapter. The adapter comprises a second priming site and an adapter barcode. In some embodiments, the second amplification primer comprises a priming sequence complementary to or identical to a sequence within the adapter, for example a second priming site. In some embodiments of the compositions and kits, the second amplification primer hybridizes to (1) a portion of an adapter attached to the polynucleotide at a distance from the first priming site, or (2) a second priming site of the polynucleotide, wherein the second priming site is at a distance from the first priming site. In some embodiments, the adapter and/or the second priming site is at a 5' end of a strand of the polynucleotide, and the first priming site is at a 3' end of the strand.

In other embodiments, the present disclosure provides methods, compositions, and kits for detecting a genomic rearrangement in a polynucleotide. The methods, compositions, and kits comprise amplifying a polynucleotide with a first amplification primer and a second amplification primer. The first amplification primer hybridizes to a first priming site of the polynucleotide, and the first amplification primer further comprises a target-specific barcode. The amplifying generates polynucleotide amplicons, comprising sequences identical or complementary to the polynucleotide of interest and the target-specific barcodes. The polynucleotide amplicons are sequenced at first and second locations by performing a first primer extension and a second primer extension. The first primer extension and the second primer extension can be performed in a same direction.

In the foregoing methods, compositions and kits, the target-specific barcode is specific to a target such as a gene, a portion of a gene, a fusion gene, a portion of a fusion gene, or other polynucleotide of interest. The fusion gene can be a known fusion gene, including a junction of a known fusion gene, and/or the fusion gene can be a suspected or hypothesized fusion gene, or a junction of such a fusion gene. The target can be a genomic rearrangement, such as deletions, insertions, inversions, and translocations in a polynucleotide of interest. In some embodiments, the target is a cDNA junction or exon junction.

In some embodiments, the second amplification primer hybridizes to a portion of the adapter, such as a second priming site, which can be a sequencing priming site of the adapter. In some embodiments, the adapted polynucleotide comprises the adapter at a 5'-end and/or the target-specific barcode at a 3'-end.

In some embodiments, the polynucleotide of interest comprises a plurality of polynucleotides of interest, and the method comprises attaching a plurality of adapters to the plurality of polynucleotides, thereby forming a plurality of adapted polynucleotides, each comprising a different adapter barcode. Alternatively or additionally, wherein the polynucleotide of interest comprises a plurality of polynucleotides of interest, and the first amplification primer comprises a plurality of first amplification primers having different target-specific primers and target-specific barcodes, thereby forming a plurality of adapted polynucleotide amplicons, each comprising a different target-specific barcode.

In some embodiments, the adapted polynucleotide amplicons are sequenced at first and second locations by performing a first primer extension and a second primer extension, wherein the first primer extension and the second primer extension are performed in a same direction. In some embodiments, the first primer extension is performed with a first sequencing primer that is complementary or identical to a portion of an adapter, such as the second priming site. In some embodiments, the second primer extension is performed with a second sequencing primer that is complementary or identical to a portion of the first amplification primer, such as a portion adjacent to the target-specific barcode or of sufficient proximity for single-end sequencing of the target-specific barcode.

Sequencing by primer extension is performed by hybridizing primers to polynucleotide amplicons; extending the primers by addition of one or more labeled nucleotides, thereby producing incorporated labeled nucleotides; and detecting the incorporated labeled nucleotides. Sequencing primers can be complementary or identical to sequences on adapters. In some embodiments, the first primer extension and the second primer extension are performed in the same direction on the polynucleotide during separate sequencing runs. In some embodiments, the sequencing is next generation sequencing (NGS) or massively parallel sequencing.

The data generated from the sequencing of the first primer extension and/or the second primer extension can be compared with a known nucleic acid sequence such as a known gDNA sequence.

The present methods, compositions, and kits are useful for the sequencing of polynucleotides, including genomic DNA (gDNA), complementary DNA (cDNA) derived from a RNA template (e.g., messenger RNA (mRNA) or microRNA (microRNA)), mitochondrial DNA (mtDNA), RNA such as mRNA, microRNA, and other polynucleotides. The polynucleotides can be of any origin, such as microbial, viral, fungal, plant, or mammalian.

In some embodiments, the present methods, compositions and kits are used to detect the presence, location, or absence of a genomic rearrangement in a polynucleotide of interest. The genomic rearrangement may be as a deletion, duplication, insertion, inversion, or translocation, and the methods, compositions, and kits can be used to detect whether a certain genomic sequence or gene has been deleted, duplicated, inserted, inverted, or translocated in a polynucleotide of interest. In some embodiments, the present methods, compositions and kits are used to detect a genomic deletion. In some embodiments, the present methods, compositions and kits are used to detect a genomic duplication. In some embodiments, the present methods, compositions and kits are used to detect a genomic insertion. In some embodiments, the present methods, compositions and kits are used to detect a genomic inversion. In some embodiments, the present methods, compositions and kits are used to detect a genomic translocation. In some embodiments, the present methods, compositions and kits are used to detect a genomic rearrangement in a polynucleotide such as gDNA or cDNA derived from RNA. In some embodiments, the genomic rearrangement has a frequency of about 100% or less, alternatively about 50% or less, alternatively about 10% or less, alternatively about 5% or less, alternatively about 1% or less. In some embodiments, the present methods further comprises detecting a genomic rearrangement using single-end sequencing of the polynucleotide amplicons, such as by identifying that genomic rearrangement based on data generated from the sequencing of the first primer extension and the second primer extension. In some embodiments, the genomic rearrangement is a translocation.

Sequencing methods are provided that can be used to detect genomic rearrangements in polynucleotides. The present methods can be used to more easily and reliably detect genomic rearrangements utilizing single-end sequencing of nucleic acids of interest. The present methods can be used in a Next Generation Sequencing (NGS) process for detection of deletions, insertions, inversions, and translocations in a polynucleotide of interest. The present methods involve sequencing a first and second primer extension in the same direction to increase the accuracy of polynucleotide rearrangement detection. The combined sequence data from the first and second primer extensions facilitates read alignment and identification of genomic rearrangements in a polynucleotide. The combination of the reads generated in the same direction allow for more accurate identification of the relative position of the nucleic acids in the polynucleotide. The present methods improve the ability of single-end sequencing processes to identify the relative positions of nucleotides in a genome, resulting in more effective resolution of structural rearrangements compared to standard single-end sequencing methods.

The present methods may be used in a high-throughput sequencing method such as a Next Generation Sequencing (NGS) process. In some embodiments, a high-throughput sequencing method comprises three steps: library preparation, immobilization, and sequencing. The polynucleotide generally is subjected to random fragmentation, and adapters are ligated to one or both ends of the fragments. The adapters may be linear adapters, circular adapters, or bubble adapters. The sequencing library fragments are immobilized on a solid support, and parallel sequencing reactions are performed to interrogate the polynucleotide sequence. The high-throughput sequencing method may employ Emulsion PCR, Bridge-PCR, or Rolling Circle amplification to provide copies of the original polynucleotide.

Polymerases tend to make errors during PCR (most frequently mis-incorporation of nucleotides) and, if these errors occur during early cycles they appear as variants in the analysis of sequencing data. Molecular barcodes can be used to distinguish PCR errors from actual variants in a polynucleotide of interest. The concept of molecular barcodes is that each polynucleotide in a pool to be amplified is attached to a unique molecular barcode. Sequence reads that have different molecular barcodes represent different original DNA molecules, while reads that have the same barcodes are the result of PCR duplication from the same original molecule. Molecular barcodes called degenerate base regions (DBR) are disclosed in U.S. Pat. No. 8,481,292 (Population Genetics Technologies Ltd.). The DBRs are random sequence tags that are attached to molecules that are present in the sample. DBRs and other molecular barcodes allow one to distinguish PCR errors during sample preparation from mutations and other variants that were present in the original polynucleotide.

Attaching Adapters to Polynucleotides

In some embodiments, a polynucleotide is attached to an adapter to form an adapted polynucleotide. An adapter can be attached to a polynucleotide before or after amplification, and in some embodiments the polynucleotide is a polynucleotide amplicon and the adapted polynucleotide is an adapted polynucleotide amplicon. The adapter can be attached by any suitable technique, such as by ligation, use of a transposase, hybridization, and/or primer extension. In some embodiments, the polynucleotide is ligated with an adapter at one or both ends. In a ligation reaction, a covalent bond or linkage is formed between the termini of two or more polynucleotides (such as a nucleic acid of interest) or oligonucleotides (such as an adapter). The nature of the bond or linkage may vary, and the ligation may be carried out enzymatically or chemically. Ligations are usually carried out enzymatically to form a phosphodiester linkage between a 5' carbon of a terminal nucleotide of one polynucleotide or oligonucleotide with 3' carbon of another polynucleotide or oligonucleotide. In some embodiments, the adapter is a Y adapter which can generate libraries with varying 5' ends and having P5 and P7 priming sites suitable for using on Illumina MiniSeq, NextSeq, and HiSeq 3000/4000 sequencing instruments.

In some embodiments, A/B adapters are attached to the polynucleotide of interest, in which an A adapter is attached to one end of a polynucleotide and a B adapter is attached to an opposite end of the polynucleotide. In some embodiments, A/B adapters are attached by random ligation, or use of a transposase, or by amplification through primer extension. It is contemplated that individual characteristics of the A adapter and the B adapter provide that each polynucleotide included in a sequencing procedure will include both an A and B adaptor (that is, one of type of adapter is attached to a 5' end and the other type of adapter is attached at the 3' end of each polynucleotide that undergoes sequencing, represented as an A/B adaptor combination). Due to the random nature of the ligation step, A/A and BB adapted polynucleotides will also be produce, and subsequent processing steps can be taken to insure that only molecules with an A/B adaptor combination are selected for and/or included in the sequencing procedure. The adapted polynucleotides can be amplified using primers directed to portions of the adapters, to increase the amount of the polynucleotide of interest, either before or after the amplification described herein for attaching a target-specific barcode. In some embodiments, adapters are attached in a manner and to a sufficient number of polynucleotides to create a fully sequenceable library for massively parallel sequencing.

In some embodiments, the adapter comprises an adapter barcode. The adapter barcode can serve any desired purpose, such as an identifier of the source or nature of the polynucleotide. A barcode generally refers to any sequence information used for identifying, grouping, or processing a polynucleotide. Barcodes can be included to identify individual reads, groups of reads, subsets of reads associated with probes, subsets of reads associated with exons, subsets of reads associated with samples or any other group, or any combination thereof. For example, sequences can be sorted (e.g., using a computer processor) by sample, exon, probe set, or a combination thereof by referencing barcode information. Barcode information may be used to assemble contigs. A computer processor can identify the barcodes and assemble the reads by organizing the barcodes together.

The polynucleotide may be obtained by any suitable mechanism. The polynucleotide of interest may be genomic deoxyribonucleic acid (gDNA), cDNA, mRNA, mitochondrial DNA, or other type. The polynucleotide may be mammalian, viral, fungal, or bacterial, or mixtures thereof. In some embodiments, a polynucleotide chain such as genomic DNA is fragmented using any suitable technique prior to attaching the adapters to the polynucleotides. As known in the art, a polynucleotide chain may be fragmented using physical fragmentation, enzymatic fragmentation, or chemical shearing fragmentation. In some embodiments, the polynucleotide is fragmented using a physical fragmentation method such as sonication, acoustic shearing, or hydrodynamic shearing. In some embodiments, the polynucleotide is fragmented using a restriction enzyme. In some embodiments, the polynucleotide is fragmented using an enzyme such as DNase I or a transposase. In some embodiments, the polynucleotide is fragmented using a chemical shearing method such as heat digestion in the presence of a metal cation. In some embodiments, the polynucleotide is randomly fragmented. In some embodiments the polynucleotide can be treated with sodium bisulfite or other chemical modifiers. In some embodiments, the polynucleotide fragments are used to populate a sequencing library.

The polynucleotide fragments may be of any suitable base length. In some embodiments, the polynucleotide fragment has a base length of about 30 to about 2,000. In some embodiments, the polynucleotide fragment has a base length of about 30 to about 800. In some embodiments, the polynucleotide fragment has a base length of about 30 to about 500. In some embodiments, the polynucleotide fragment has a base length of about 100 to about 800. In some embodiments, the polynucleotide fragment has a base length of about 200 to about 600.

After fragmentation, one or more adapters may be attached to the polynucleotide fragment. In some embodiments, the adapter is a linear adapter, a circular adapter, or a bubble adapter. In some embodiments, the polynucleotide is ligated to at least one circular adapter. In some embodiments, the polynucleotide fragments are contacted with circular adapters to generate circular polynucleotide molecules. In some embodiments, only circular polynucleotide molecules are amplified during the amplification process. In any of these embodiments, the adapter can comprise an adapter barcode.

Amplification of the Target Polynucleotide

The present method comprises amplifying a polynucleotide before and/or after it is attached to an adapter. In some embodiments, an adapter is located at a 5'-end of a sequence of interest in the polynucleotide, and the adapter provides a priming site for amplification of the sequence of interest. The adapted polynucleotide is amplified using a first amplification primer and a second amplification primer. The first amplification primer has sequence specificity for a target sequence in the polynucleotide, and is capable of hybridizing to a portion of the target sequence (a polynucleotide of interest). The second amplification primer is capable of hybridizing to a priming site of the adapter or to a target-specific priming site of the polynucleotide of interest. During the amplification step, the first amplification primer hybridizes to the target sequence and the second primer hybridizes to the sequence priming site on the adapter. In some embodiments, the first amplification primer hybridizes at the 5'-end of the adapted polynucleotide. The primers of the present method should be sufficiently large to provide adequate hybridization with the target sequence of the polynucleotide.

For amplification, the polynucleotide of interest is hybridized with a first amplification primer comprising a target-specific barcode. The first amplification primer is complementary to at least a portion of the polynucleotide. The first amplification primer hybridizes to a first priming site of the polynucleotide. The polynucleotide comprises the target sequence at the 3'-end, optionally followed by an adapter. The first amplification primer hybridizes to an adapted polynucleotide if the target sequence is present in the adapted polynucleotide, thereby allowing selective amplification and detection of the target sequence. The first amplification primer can be complementary to and/or hybridizes to a genomic rearrangement, such as a deletion, insertion, inversion, or translocations in a polynucleotide of interest. In some embodiments, the first amplification primer is complementary and/or hybridizes to cDNA junction or exon junction. In some embodiments, the first amplification primer is complementary and/or hybridizes to a fusion gene, such as a known fusion gene, including a junction of a known fusion gene, and/or a suspected or hypothesized fusion gene, or a junction of a suspected or hypothesized fusion gene.

The second amplification primer hybridizes to the polynucleotide or to an adapter at a distance from the first priming site. In some embodiments, the second amplification primer hybridizes to a portion of an adapter attached to the polynucleotide at a distance from the first priming site. In some embodiments, the second amplification primer hybridizes to a second priming site of the polynucleotide, wherein the second priming site is at a distance from the first priming site.

A polynucleotide of interest may be amplified using any suitable method. In some embodiments, the polynucleotide is amplified using polymerase chain reaction (PCR). In general, PCR comprises denaturation of polynucleotide strands (e.g., DNA melting), annealing of primers to the denatured polynucleotide strand, and extension of primers with a polymerase to synthesize the complementary polynucleotide. The process generally requires a DNA polymerase, forward and reverse primers, deoxynucleoside triphosphates, bivalent cations, and a buffer solution. In some embodiments, the polynucleotide is amplified by linear amplification. In some embodiments, the polynucleotide is amplified using Emulsion PCR, Bridge-PCR, or Rolling Circle amplification. The amplified polynucleotides may be analyzed to determine the order of base pairs using a suitable sequencing method.

In some embodiments, one or more of the primers or polynucleotides are immobilized on a solid support. Immobilization of the amplification primer and/or polynucleotide can facilitate washing of the polynucleotides to remove any undesired species (e.g., deoxynucleotides). In some embodiments, the polynucleotide comprises one or more adapters which attach to the solid support, rendering the polynucleotide immobilized on the support. In some embodiments, the polynucleotide is immobilized on the surface of a flow cell or a glass slide. In some embodiments, the polynucleotide is immobilized on a microtitre well or magnetic bead. In some embodiments, the solid support may be coated with a polymer attached to a functional group or moiety. In some embodiments, the solid support may carry functional groups such as amino, hydroxyl, or carboxyl groups, or other moieties such as avidin or streptavidin for attachment of adapters.

The polynucleotide amplicons can be adapted polynucleotide amplicons. In some embodiments, an adapted polynucleotide or a polynucleotide amplicon comprises a binding partner, such as a biotin moiety. A polynucleotide can be attached to an adapter comprising a binding partner, or a polynucleotide can be amplified using one or more primers comprising a binding partner. In some embodiments, the present methods comprise forming a complex between reciprocal binding partners, such as a biotinylated primer extension product and solid-supported avidin or streptavidin. The methods can also include enriching a sample containing the adapted polynucleotide comprising a binding partner by binding to a reciprocal binding partner. The proteins avidin and streptavidin form exceptionally tight complexes with biotin and certain biotin analogs. In general, when biotin is coupled to a second molecule through its carboxyl side chain, the resulting conjugate is still tightly bound by avidin or streptavidin. The second molecule is said to be "biotinylated" when such conjugates are prepared. In general, the present methods involve complexation of a biotinylated nucleic acid to avidin or streptavidin, followed by detection, analysis, and/or use of the complex. In some embodiments, a biotinylated polynucleotide is immobilized on a flow cell coated with streptavidin or a metallic bead coated with streptavidin. In some embodiments of the present methods, compositions and kits, target-specific primers (e.g., the first amplification primers) may be attached to a binding partner such as a biotin moiety to allow for selection or purification by binding to a reciprocal binding partner such as streptavidin or avidin. Useful binding partners include biotin:avidin, biotin:streptavidin, antibody:antigen, and complementary nucleic acids. In some embodiments, the target-specific primers may include a binding partner such as biotin to allow for capture of the selectively amplified pool.

Preparation of polynucleotides for next generation sequencing often employs target enrichment prior to next-generation sequencing, and one or more target enrichment protocols can be included in the present methods. By enriching for one or more desired target polynucleotides, the sequencing can be more focused with reduced effort and expense and/or with high coverage depth. Examples of current enrichment protocols for next generation sequencing include hybridization-based capture protocols such as SureSelect Hybrid Capture from Agilent and TruSeq Capture from Illumina. Other examples include PCR-based protocols such as HaloPlex from Agilent; AmpliSeq from ThermoFisher; TruSeq Amplicon from Illumina; and emulsion/digital PCR from Raindance.

In some embodiments, a library of polynucleotides having universal adapters at both ends is amplified using a method such as PCR. Target-specific primers comprising a custom adapter can be added to the reaction to allow for amplification of a target sequence. In such an embodiment, two pools of fragments are generated: (a) a pool of fragments with universal adapters at both ends, and (b) a pool of fragments generated by selective amplification with a sequence specific adapter at one or both ends. The mixed pool of fragments can be subjected to target enrichment if desired.

In some embodiments of the present methods, compositions and kits, more than one target-specific primer is employed or provided for amplification. Amplification can be single-plex or multiplex. Multiplex PCR is a molecular biology technique for the amplification of multiple nucleic acid targets in a single PCR experiment. Kits for multiplex amplification of target sequences are available from Multiplicom NV.

In some embodiments of the present methods, compositions and kits, polynucleotide amplicons are used in transposable element (TE) protocols. Adapters can be attached to the amplicons by using a transposase to insert transposons comprising adapters, thereby providing adapters at the ends of fragments of the amplicons. In some embodiments, polynucleotides may be fragmented and barcoded at the same time. For example, a transposase (e.g., NEXTERA) may be used to fragment a polynucleotide and add a barcode to the polynucleotide.

Fusion Genes

The target-specific primer can be complementary or identical to a portion of any known or suspected fusion gene. By way of example, the target-specific primer can be complementary or identical to any of the fusion genes disclosed in US20100279890, US20140120540, US20140272956, or US20140315199. By way of further example, the target-specific primer can be complementary or identical to any of the following fusion genes: BCR-ABL, EML4-ALK, TEL-AML1, AML1-ETO, and TMPRSS2-ERG. Alternatively, a target-specific primer can be complementary or identical to a newly discovered fusion gene, or a junction of such a fusion gene. Alternatively, a target-specific primer can be complementary or identical to a suspected or hypothesized fusion gene, or a junction of such a fusion gene.

In some embodiments, the present methods, compositions and kits comprise a plurality of target-specific primers for different fusion genes. For instance, a plurality of target-specific primers can comprise a first target-specific primer for a BCR-ABL junction, and a second target-specific primer for a EML4-ALK. In some embodiments, the present methods, compositions and kits comprise a plurality of target-specific primers for a single fusion gene, including for a plurality of junctions of a single fusion gene. For instance, a plurality of target-specific primers can comprise a first target-specific primer for a first EML4-ALK junction, and a second target-specific primer for a second EML4-ALK junction. The present methods, compositions and kits can comprise a third target-specific primer, a fourth target-specific primer, a fifth target-specific primer, up to a twentieth target-specific primer, or even more target-specific primers.

Sequencing of the Target Sequence

After amplification, adapted polynucleotide amplicons can be sequenced. For example, sequencing may be performed by a first primer extension and a second primer extension of the adapted polynucleotide amplicons generated during amplification. In some embodiments, the first and second primer extensions are performed in the same direction on an individual amplicon or on a set of identical amplicons. The first primer extension determines sequencing by detecting bases that are incorporated as a result of extension from the first primer (and other primers), allowing the determination of at least a portion of a target sequence of the polynucleotide, particularly those located 5' to an adapter. Adapted polynucleotides can contain a sequencing priming site, such as P5 or P7 primary sites. In some embodiments, the first primer extension can also be used to detect the sequence of the adapter barcode. The second primer extension determines sequencing by detecting bases that are incorporated as a result of extension from the second primer, allowing for detection of the target-specific barcode. Sequencing of the target-specific barcode is used to substantiate the presence and/or location of the gene or other polynucleotide that is specific to the target-specific barcode in the polynucleotide of interest.

In some embodiments, sequencing is performed by massive parallel sequencing using sequencing-by synthesis with reversible dye terminators. In some embodiments, sequencing is performed by massive parallel sequencing using sequencing-by-ligation. In some embodiments, sequencing is performed by single molecule sequencing. In some embodiments, sequencing is performed using pyrosequencing.

The polynucleotide may be sequenced using any suitable reaction method. In some embodiments, a single reaction cycle may be done using a single nucleotide (i.e., a nucleotide corresponding to G, A, T or C) and the method involves detecting whether a nucleotide is incorporated. If a nucleotide is incorporated, then the identity of the nucleotide becomes known. In such embodiments, the method may involve cycling through all four nucleotides (i.e., nucleotides corresponding to G, A, T and C) in succession and one of the nucleotides should be incorporated. In such embodiments, the addition of the nucleotide may be detected by detecting pyrophosphate release, proton release or fluorescence, for example, methods for which are known. For example, in some embodiments, the chain terminator nucleotide may be a terminal phosphate labeled fluorescent nucleotide (i.e., a nucleotide that has a fluorophore attached to the terminal phosphate) and the identifying step comprises reading fluorescence. In other embodiments, the chain terminator nucleotide may be a fluorescent nucleotide that comprises a quencher on a terminal phosphate. In such embodiments, incorporation of the nucleotide removes the quencher from the nucleotide, thereby allowing the fluorescent label to be detected. In other embodiments, the terminal phosphate labeled chain terminator nucleotide may be labeled on the terminal phosphate with a mass tag, charge label, charge blockade label, chemiluminescent label, redox label, or other detectable label.

In some embodiments, a single reaction cycle may be done using all four nucleotides (i.e., nucleotides corresponding to G, A, T and C), each labeled with different fluorophores. In such embodiments, the sequencing step may comprises adding the four chain terminators corresponding to G, A, T and C to the amplified polynucleotide, wherein the four chain terminators comprise different fluorophores. In such embodiments, the identifying step may comprise identifying which of the four chain-terminator is added to the end of the primer.

The sequencing step can be performed using single-end sequencing, i.e., the first primer extension and the second primer extension sequences are read in the same direction. In some embodiments, a genomic analyzer that is single-end enabled is used to sequence the polynucleotide. In some embodiments, the method comprises continuously monitoring the sequencing reactions (i.e., base incorporation) in real time. This may simply be achieved by performing the chain extension and detection, or signal-generation, reactions simultaneously by including the "detection enzymes" in the chain extension reaction mixture. In some embodiments, the chain extension reaction is first performed separately as a first reaction step, followed by a separate "detection" reaction where the primer extension products are subsequently detected.

Analysis of the Sequencing Data

A genomic rearrangement may be identified based on data generated from sequencing of the first primer extension and the second primer extension. The present method comprises identifying a genomic rearrangement in a polynucleotide based on data generated from sequencing the first primer extension and the second primer extension. Sequencing data from the first primer extension provides the sequence of base pairs of the target sequence. Sequencing data from the second primer extension provides the sequence of base pairs for the adapter, which can be used to indicate or substantiate the presence of the target sequence, since the adapter is designed to hybridize specifically with the target sequence in the polynucleotide sample. The combined data provided by the two primer extensions provides positional information for determining any genomic rearrangement in the polynucleotide.

The data generated from the first and second primer extensions is compared to a reference sample. Any difference between the reference sample and the data generated from the first and second primer extensions indicates that a genomic rearrangement may be present in the sample under study. The sequence of the reference sample and the sequences generated from the first primer extension and second primer extension relative to the reference sample can be used to identify the type and location of any genomic rearrangement.

The present methods, compositions and kits may be used to detect any sequence of interest, including those associated with common deletion syndromes.

Example 1

FIG. 1 illustrates a method of preparing a polynucleotide for sequencing by attaching adapters and barcodes to the polynucleotides, as well as the adapted polynucleotide and adapted polynucleotide amplicon generated by the present techniques. The adapted polynucleotide can be used for detecting a fusion event using selective gene amplification in accordance with an embodiment of the invention. In FIG. 1, an adapted polynucleotide 102 comprises a nucleic acid of interest, in this case, the junction of a fusion gene. An adapted polynucleotide 102 comprises a first gene 104 and a second gene 106. The adapted polynucleotide 102 also comprises adapters 108, 110 at each end. The adapters can be attached by any suitable procedure, such as by ligation. At least one of the adapters comprises an adapter barcode 112 which can be a molecular barcode or a sample barcode.

At period A, the adapted polynucleotide is prepared for target-specific amplification. The adapted polynucleotide can be denatured to provide a single-stranded polynucleotide, or a double-strand polynucleotide can be provided for amplification. In some embodiments, the adapted polynucleotide is amplified in a non-specific manner (for example, by amplifying the adapted polynucleotides with a primer complementary to a priming site on the adapter attached to the members of the library of adapted polynucleotides. In some embodiments, the adapted polynucleotide is enriched as discussed above, generally before the amplification of the adapted polynucleotides.

The adapted polynucleotide is prepared for contact with a first amplification primer 114 that comprises a target-specific primer 116. The target-specific primer 116 is complementary to a sequence known or suspected to be present in the adapted polynucleotide, for example, a sequence within a second gene 106. The first amplification primer 114 also comprises a target-specific barcode 118, which is specific to a portion of a gene or other target known or suspected of being present in a sample being analyzed or in the polynucleotide of interest. In this context, gene-specific does not mean that it is complementary to the gene, but rather that the barcode is specifically associated with the gene, so that detecting the sequence of the gene-specific barcode reliably indicates that the associated sequence is present.

At period B, the adapted polynucleotide is subjected to amplification in the presence of the first amplification primer 114 and a second amplification primer 120 to generate a library of adapted polynucleotide amplicons. The adapted polynucleotide amplicons comprise a nucleic acid of interest, an adapter or its complement, and a gene-specific barcode or its complement. For ease of illustration, FIG. 1 shows one set of the first amplification primer 114 and a second amplification primer 120, though the amplification reaction can employ a large number of target-specific primers for various sequences and can generate amplicons of a large number of nucleic acids of interest. In some embodiments, the adapted polynucleotide is enriched from a pool of polynucleotides, such as where the tag includes biotin or another binding partner.

In some embodiments (which may be in addition or instead of enrichment), a polynucleotide (including an adapted polynucleotide) can be amplified with an outside or inside primer or nested primers. In such embodiments, an outside primer or primer used in an earlier round of amplification is a target-specific primer that need not include a target-specific barcode. An inside primer or primer for a subsequent round of amplification is also a target-specific primer, and it comprises a target-specific barcode. In general, nested PCR refers to one or more later rounds of PCR amplification using one or more new primers that bind internally, by at least one base pair, to the primers used in a earlier round. Nested PCR reduces the number of unwanted amplification targets by amplifying, in subsequent reactions, only those amplification products from the previous one that have the correct inside sequence. Nested PCR typically entails designing primers completely inside the previous outside primer binding sites.

The adapted polynucleotide amplicons can then be sequenced. In some embodiments, a first sequencing primer 122 complementary to a first priming site 124 of the adapter 108 is employed to perform a first primer extension for the sequencing of at least the first gene 104. Labeled nucleotides are added to the primer in the sequencing reaction, and a first extended sequence 126 complementary to the adapted polynucleotide amplicon is generated, providing sequence information regarding the adapted polynucleotide. The first primer extension occurs at a first location of the adapted polynucleotide amplicon. The first priming site 124 can generally be 5' or 3' to the adapter barcode, depending on whether one wishes to sequence the adapter barcode together with or separately from the first gene 104. A second sequencing primer 128 is used to perform a second primer extension for the sequencing of at least the gene-specific barcode 118. The second sequencing primer 128 is complementary to a portion 130 of the first amplification primer 114 which is 3' of the gene-specific barcode 118 and 5' of a target-specific sequence 116. Labeled nucleotides are added to the primer in the sequencing reaction, and a second extended sequence 132 complementary to the gene-specific barcode is generated, providing sequence information regarding the gene-specific barcode. As noted above, the ordinal numbers first and second do not mean that a first primer is used before a second primer; instead they are used to distinguish different primers from each other.

At time period C, the data from the sequencing reactions is processed and interpreted. In some embodiments, the first extended sequence 126 is determined to be a sequence of a first gene, and the second extended sequence 132 is determined to be a sequence of a gene-specific barcode associated with a second gene. Based on these determinations, the data is interpreted as indicating the presence of a fusion gene among the nucleic acid of interest. The fusion gene contains portions of a first gene and a second gene, and its presence is determined even without directly sequencing the second gene 106 itself.

Example 2

Figure 2:
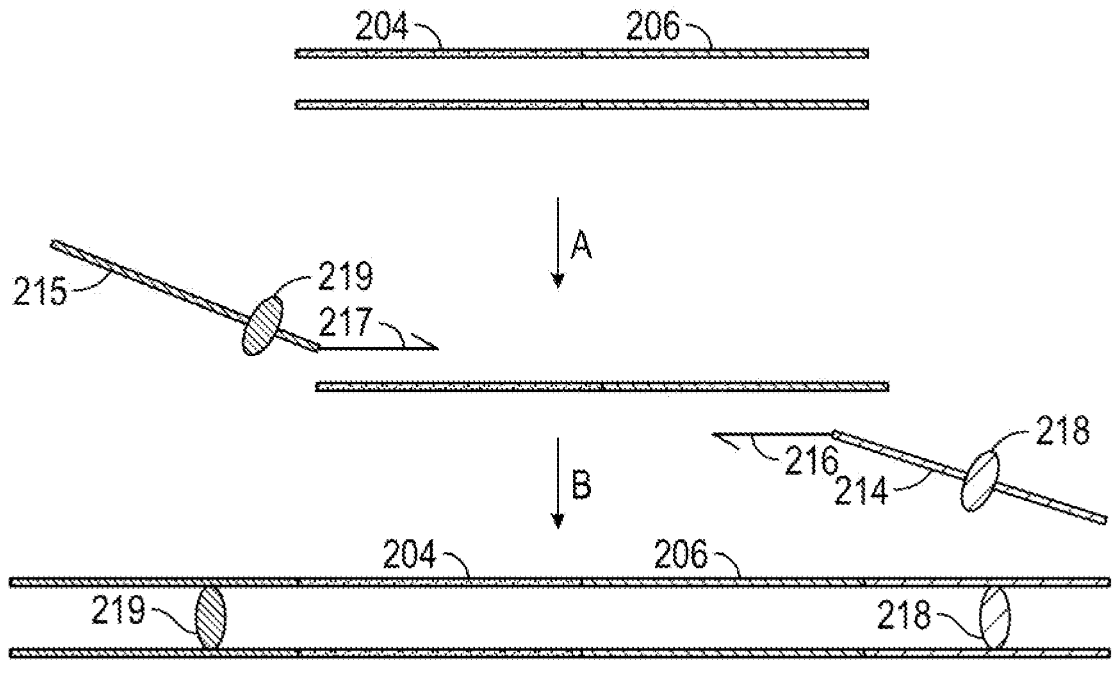
FIG. 2 illustrates another embodiment of the methods of preparing polynucleotides for sequencing.
Figure 2:
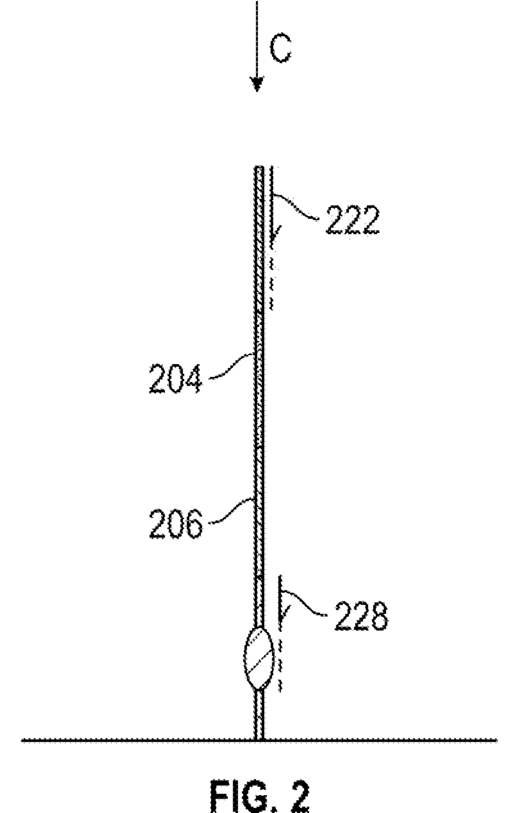

FIG. 2 illustrates that a polynucleotide can be amplified with a target-specific primer with or without earlier attachment of an adapter. The polynucleotide can be prepared for sequencing by attaching adapters to the polynucleotides, followed by target-specific (workflow on left of FIG. 2), or the as well as the adapted polynucleotide and adapted polynucleotide amplicon generated by the present techniques. The adapted polynucleotide can be used for detecting a genomic rearrangement or other fusion event using selective gene amplification in accordance with an embodiment of the invention. In FIG. 2, a polynucleotide 202 comprises a nucleic acid of interest, in this case, the junction of a fusion gene. A polynucleotide 102 comprises a first gene 204 and a second gene 206.

At period A, the polynucleotide is prepared for target-specific amplification. The polynucleotide can be denatured to provide a single-stranded polynucleotide, or a double-strand polynucleotide can be provided for amplification. In some embodiments, the polynucleotide is amplified in a non-specific manner (for example, by amplifying the polynucleotides with a primer complementary to a priming site on the adapter attached to the members of the library of adapted polynucleotides. In some embodiments, the polynucleotide is enriched as discussed above, generally before the amplification of the polynucleotides.

The polynucleotide is prepared for contact with a first amplification primer 214 that comprises a target-specific primer 216. The target-specific primer 216 is complementary to a sequence known or suspected to be present in the polynucleotide, for example, a sequence within gene 206. The first amplification primer 214 also comprises a gene-specific barcode 218, which is specific to a portion of a gene known or suspected of being present in a sample being analyzed or in the polynucleotide of interest. The polynucleotide is also prepared for contact with a second amplification primer 215 that comprises a target-specific primer 217. The target-specific primer 217 is complementary to a sequence known or suspected to be present in the polynucleotide, for example, a sequence within gene 204. The second amplification primer 215 also comprises a barcode 219, such as a target-specific barcode, a sample barcode, a molecular barcode, or other barcode, or a combination of barcodes. One or both of the first and second amplification primers may comprise an adapter.

At period B, the polynucleotide is subjected to amplification in the presence of the first amplification primer 214 and the second amplification primer 215 to generate a library of polynucleotide amplicons. The polynucleotide amplicons comprise a nucleic acid of interest and a target-specific barcode or its complement. The polynucleotide amplicons can be adapted polynucleotide amplicons, in which they comprise a nucleic acid of interest, an adapter or its complement, and a target-specific barcode or its complement. For ease of illustration, FIG. 2 shows one set of the first amplification primer 214 and a second amplification primer 215, though the amplification reaction can employ a large number of target-specific primers for various sequences and can generate amplicons of a large number of nucleic acids of interest.

The polynucleotide amplicons can then be sequenced, or they can be subjected to additional processing steps such as enrichment, further amplification, and/or attachment of an adapter. For example, adapters can be attached to each end of the amplicons so that the adapted polynucleotide amplicons have sequencing priming sites and/or can be attached to a solid support. In time period C, a polynucleotide amplicon has hybridized to a primer attached to a solid support, and the primer has been extended to provide the complement of the polynucleotide amplicon attached to the support. A first sequencing primer 222 complementary to a first priming site 224 of the adapter 208 is employed to perform a first primer extension for the sequencing of at least the first gene 204. Labeled nucleotides are added to the primer in the sequencing reaction, and a first extended sequence 226 complementary to the adapted polynucleotide amplicon is generated, providing sequence information regarding the adapted polynucleotide. The first primer extension occurs at a first location of the adapted polynucleotide amplicon. The first priming site 224 can generally be 5' or 3' to the adapter barcode, depending on whether one wishes to sequence the adapter barcode together with or separately from the first gene 204. A second sequencing primer 228 is used to perform a second primer extension for the sequencing of at least the gene-specific barcode 218. The second sequencing primer 228 is complementary to a portion 230 of the first amplification primer 214 which is 3' of the gene-specific barcode 218 and 5' of a target-specific sequence 216. Labeled nucleotides are added to the primer in the sequencing reaction, and a second extended sequence 232 complementary to the gene-specific barcode is generated, providing sequence information regarding the gene-specific barcode. As noted above, the ordinal numbers first and second do not mean that a first primer is used before a second primer; instead they are used to distinguish different primers from each other.

At time period C, the data from the sequencing reactions is processed and interpreted. In some embodiments, the first extended sequence 226 is determined to be a sequence of a first gene, and the second extended sequence 232 is determined to be a sequence of a gene-specific barcode associated with a second gene. Based on these determinations, the data is interpreted as indicating the presence of a fusion gene among the nucleic acid of interest. The fusion gene contains portions of a first gene and a second gene, and its presence is determined even without directly sequencing the second gene 206 itself.

EXEMPLARY EMBODIMENTS

Embodiment 1. A method of preparing a polynucleotide for sequencing by attaching a target-specific barcode, the method comprising: amplifying a polynucleotide with a first amplification primer and a second amplification primer, wherein the first amplification primer hybridizes to a first priming site of the polynucleotide, and the first amplification primer comprises a target-specific barcode; wherein the amplifying generates polynucleotide amplicons, wherein the polynucleotide amplicons comprise sequences identical or complementary to the polynucleotide of interest and the target-specific barcode.

Embodiment 2. The method of embodiment 1, wherein the second amplification primer hybridizes to (1) a portion of an adapter attached to the polynucleotide at a distance from the first priming site, or (2) a second priming site of the polynucleotide, wherein the second priming site is at a distance from the first priming site.

Embodiment 3. The method of embodiment 1, further comprising attaching an adapter to the polynucleotide at a distance from the first priming site, wherein the adapter comprises a second priming site.

Embodiment 4. The method of embodiment 3, wherein the adapter further comprises an adapter barcode, wherein the adapter barcode is a sample barcode or a molecular barcode.

Embodiment 5. The method of any of the foregoing embodiments, wherein the first priming site is a portion of a fusion gene, and the target-specific barcode is specific for the portion of the fusion gene.

Embodiment 6. The method of embodiment 5, wherein the portion of the fusion gene is a junction of the fusion gene.

Embodiment 7. The method of any of the foregoing embodiments, wherein the polynucleotide is genomic (gDNA) or complementary DNA (cDNA) derived from a RNA template.

Embodiment 8. The method of any of the foregoing embodiments, wherein the polynucleotide of interest comprises a plurality of polynucleotides of interest, and the method comprises attaching a plurality of adapters to the plurality of polynucleotides, thereby forming a plurality of adapted polynucleotides, each of the plurality of adapted polynucleotides comprising a different molecular barcode.

Embodiment 9. The method of any of the foregoing embodiments, wherein the polynucleotide of interest comprises a plurality of polynucleotides of interest, and the first amplification primer comprises a plurality of first amplification primers having different target-specific primers and different target-specific barcodes, thereby forming a plurality of adapted polynucleotide amplicons, each of the plurality of adapted polynucleotide amplicons comprising a different target-specific barcode.

Embodiment 10. The method of any of the foregoing embodiments, wherein the polynucleotide amplicons or adapted polynucleotide comprise a binding partner, such as a biotin moiety.

Embodiment 11. The method of any of the foregoing embodiments, further comprising sequencing the polynucleotide amplicons at first and second locations by performing a first primer extension and a second primer extension, wherein the first primer extension and the second primer extension are performed in a same direction. The sequencing at the first location can provide a sequence of at least a portion of the polynucleotide of interest and the sequencing at the second location can provide a sequence of the target-specific barcode.

Embodiment 12. The method of embodiment 11, wherein the first primer extension and the second primer extension are performed in the same direction on the polynucleotide during separate sequencing runs.

Embodiment 13. The method of embodiment 11, wherein the sequencing is next generation sequencing (NGS) or massively parallel sequencing.

Embodiment 14. The method of any of the foregoing embodiments, further comprising detecting a genomic rearrangement using single-end sequencing of at least one of the polynucleotide amplicons, such as by identifying that genomic rearrangement based on data generated from the sequencing of the first primer extension and the second primer extension.

Embodiment 15. The method of embodiment 14, wherein the genomic rearrangement has a frequency of about 10% or less, alternatively 5% or less.

Embodiment 16. The method of embodiment 14, wherein the genomic rearrangement is a translocation.

Embodiment 17. The method of embodiment 14, wherein the data generated from the sequencing of the first primer extension is compared with a known nucleic acid sequence such as a known gDNA sequence to determine a genomic rearrangement.

Embodiment 18. A method of preparing a library of polynucleotides for sequencing by attaching a target-specific barcode, the method comprising: amplifying a pool of polynucleotides using a first set of amplification primers and a second set of amplification primers, wherein a first set of amplification primers hybridize to a plurality of different sequences within the pool of polynucleotide, wherein each of the first set of amplification primers comprises a different target-specific barcode.

Embodiment 19. The method of embodiment 18, further comprising: generating a library of adapted polynucleotides, wherein each adapted polynucleotide comprises an adapter attached to a polynucleotide, and the adapter comprises a second priming site and an adapter barcode.

Embodiment 20. The method of embodiment 19, wherein the second set of amplification primers hybridize to a second priming site on the adapter, thereby generating adapted polynucleotide amplicons.

Embodiment 21. The method of embodiment 18, further comprising sequencing each of the plurality of adapted polynucleotide amplicons at two locations by performing a first primer extension and a second primer extension, wherein the sequencing of the first primer extension and the second primer extension are performed in the same direction for each of the polynucleotide amplicons.

Embodiment 22. The method of embodiment 21, further comprising: identifying a genomic rearrangement based on data generated from the sequencing of the first primer extension and the second primer extension.

Embodiment 23. A composition or kit for detecting a genomic rearrangement in a polynucleotide having a first binding site, the composition or kit comprising: a first amplification primer comprising a target-specific primer and a target-specific barcode; and a second amplification primer.

Embodiment 24. The composition or kit of embodiment 23, further comprising: an adapter comprises a second priming site and an adapter barcode, and wherein the second amplification primer comprises a priming sequence complementary to or identical to a sequence within the adapter.

Embodiment 25. The composition or kit of embodiment 23, wherein the second amplification primer hybridizes to (1) a portion of an adapter attached to the polynucleotide at a distance from the first priming site, or (2) a second priming site of the polynucleotide, wherein the second priming site is at a distance from the first priming site.

Embodiment 26. The composition or kit of embodiment 24, wherein the adapter and/or the second priming site is at a 5' end of a strand of the polynucleotide, and the first priming site is at a 3' end of the strand.

Embodiment 27. A method of detecting a genomic rearrangement in a polynucleotide, the method comprising: amplifying a polynucleotide with a first amplification primer and a second amplification primer, wherein the first amplification primer hybridizes to a first priming site of the polynucleotide, and the first amplification primer further comprises a target-specific barcode, wherein the amplifying generates polynucleotide amplicons, comprising sequences identical or complementary to the polynucleotide of interest and the target-specific barcodes; and sequencing the polynucleotide amplicons at first and second locations by performing a first primer extension and a second primer extension, wherein the first primer extension and the second primer extension are performed in a same direction.

Embodiment 28. The method of embodiment 27, wherein the sequencing at the first location provides a sequence of at least a portion of the polynucleotide of interest and the sequencing at the second location provides a sequence of the target-specific barcode.

Embodiment 29. The method of embodiment 27 or 28, wherein the first primer extension and the second primer extension are performed in the same direction on the polynucleotide during separate sequencing runs.

Embodiment 30. The method of any of embodiments 27 to 39, wherein the sequencing is next generation sequencing (NGS) or massively parallel sequencing.

Embodiment 31. The method of any of embodiments 27 to 30, further comprising detecting a genomic rearrangement using single-end sequencing of at least one of the polynucleotide amplicons, such as by identifying that genomic rearrangement based on data generated from the sequencing of the first primer extension and the second primer extension.

Embodiment 32. The method of embodiment 31, wherein the genomic rearrangement has a frequency of about 10% or less.

Embodiment 33. The method of embodiment 31 or 32, wherein the genomic rearrangement is a translocation.

Embodiment 34. The method of any of embodiments 27 to 33, wherein the data generated from the sequencing of the first primer extension is compared with a known nucleic acid sequence such as a known gDNA sequence to determine a genomic rearrangement.

In view of this disclosure it is noted that the methods can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

We claim:

1. A composition for detecting a genomic rearrangement in a target polynucleotide having a first binding site, the composition comprising:

a target-specific first amplification primer comprising a target-specific primer, a second sequencing priming site or complement thereof, and a target-specific barcode; and a second amplification primer, wherein the second amplification primer hybridizes to (1) a portion of an adapter attached to the target polynucleotide at a distance from the first priming site, or (2) a second priming site of the target polynucleotide, wherein the second priming site is at a distance from the first priming site;

wherein the second amplification primer or the adapter comprises a first sequencing priming site or complement thereof, and a barcode; and wherein amplification of the target polynucleotide with the first and second amplification primers generates polynucleotide amplicons comprising first and second sequencing priming sites for first and second primer extensions in a same direction.

2. The composition of claim 1, further comprising:

an adapter comprises the second sequencing priming site or complement thereof, and the barcode is an adapter barcode, and wherein the second amplification primer comprises a priming sequence complementary to or identical to a sequence within the adapter.

3. The composition of claim 1, wherein the first priming site is a portion of a fusion gene, and the target-specific barcode is specific for the portion of the fusion gene.

4. The composition of claim 3, wherein the portion of the fusion gene is a junction of the fusion gene.

5. The composition of claim 1, wherein the composition comprises a plurality of adapters, wherein each of the adaptors comprises a second priming site and a different molecular barcode.

6. The composition of claim 1, wherein the composition comprises a plurality of the first amplification primers having different target-specific primers and different target-specific barcodes.

7. A kit for detecting a genomic rearrangement in a target polynucleotide having a first binding site, the kit comprising:

a target-specific first amplification primer comprising a target-specific primer, a second sequencing priming site or complement thereof, and a target-specific barcode; and a second amplification primer, wherein the second amplification primer hybridizes to (1) a portion of an adapter attached to the target polynucleotide at a distance from the first priming site, or (2) a second priming site of the target polynucleotide, wherein the second priming site is at a distance from the first priming site;

wherein the second amplification primer or the adapter comprises a first sequencing priming site or complement thereof, and a barcode; and wherein amplification of the target polynucleotide with the first and second amplification primers generates polynucleotide amplicons comprising first and second sequencing priming sites for first and second primer extensions in a same direction.

8. The kit of claim 7, further comprising:

an adapter comprises the second sequencing priming site or complement thereof, and the barcode is an adapter barcode, and wherein the second amplification primer comprises a priming sequence complementary to or identical to a sequence within the adapter.

9. The kit of claim 7, wherein the first priming site is a portion of a fusion gene, and the target-specific barcode is specific for the portion of the fusion gene.

10. The kit of claim 9, wherein the portion of the fusion gene is a junction of the fusion gene.

11. The kit of claim 8, wherein the adaptor comprises a plurality of adapters, wherein each of the adaptors comprises a different molecular barcode.

12. The kit of claim 7, wherein the first amplification primer comprises a plurality of first amplification primers having different target-specific primers and different target-specific barcodes.

13. The kit of claim 7, further comprising a first sequencing primer complementary to the first priming site for performing a first primer extension.

14. The kit of claim 13, further comprising a second sequencing primer complementary to a second priming site for performing a second primer extension.

15. The kit of claim 14, wherein the first sequencing primer extension and the second sequencing primer extension are performed in a same direction.

16. The composition of claim 1, wherein the target-specific first amplification primer comprises the second sequencing priming site, and the second amplification primer comprises a complement of the first sequencing priming site; or the target-specific first amplification primer comprises a complement of the second sequencing priming site, and the second amplification primer comprises the first sequencing priming site.

17. The kit of claim 7, wherein the target-specific first amplification primer comprises the second sequencing priming site, and the second amplification primer comprises a complement of the first sequencing priming site; or the target-specific first amplification primer comprises a complement of the second sequencing priming site, and the second amplification primer comprises the first sequencing priming site.

* * * * *